United States Patent [19]

Nalebuff

[11] 4,243,651
[45] Jan. 6, 1981

[54] ALLERGY TEST

[76] Inventor: Donald J. Nalebuff, 89 Lake Shore Dr., Oakland, N.J. 07436

[21] Appl. No.: 896,135

[22] Filed: Apr. 13, 1978

[51] Int. Cl.² ............................................. G01N 33/16
[52] U.S. Cl. ......................................... 424/1; 424/12; 23/230 B
[58] Field of Search ................... 424/1, 12; 23/230 B

*Primary Examiner*—Benjamin R. Padgett
*Assistant Examiner*—Christine M. Nucker
*Attorney, Agent, or Firm*—Ostrolenk, Faber, Gerb & Soffen

[57] ABSTRACT

A modified RAST test is used to determine a safe initial immunotherapy dosage. The dosage is inversely proportional to the RAST score.

7 Claims, No Drawings

ALLERGY TEST

BACKGROUND OF THE INVENTION

In 1966 and early 1967, two teams of investigators, working independently in the United States and in Sweden, were able to define the exact nature of the skin sensitizing antibody. The antibody proteins were found to belong to a new class of immunoglobulins which were officially designated immunoglobulin E in 1968. Within months after the discovery of the nature of IgE, new radioimmunoassays were developed for its detection.

Radioimmunoassays have earned a definitive place in clinical laboratory practice and are currently used for the detection of vitamins, enzyme systems, viruses, drugs, and at least 20 polypetide hormones. The assays derived their fundamental value from two separate properties—their sensitivity and their specificity. Any specific substance against which a specific antibody can be produced can be measured at concentrations to a billionth of a milligram.

There are two commercially available radioimmunoassays which are used in the diagnosis and management of allergy. They are the PRIST test and the RAST test.

The PRIST test measures total IgE. A paper disc to which an anti-IgE has been bound is incubated with a drop of the patient's serum. This disc binds all of the IgE in the sample. The disc is then washed to remove extraneous materials and radioactively labelled anti-IgE is added for a second incubation. During this time, the labeled anti-IgE reacts with IgE molecules previously bound to the disc and after a final washing step, the amount of radioactivity bound to the disc is measured in a gammacounter. The amount of radioactivity binding the test serum is then compared to the binding obtained by serial dilutions of a PRIST reference standard known to contain exactly 100 units of IgE. The use of a suitable reference standard is a basic requirement of all radioimmunoassay determinations because there can be unexpected variables based on changes in incubation time, changes in room temperature, and decay in the amount of radioactivity bound to the anti-IgE used in the second stage.

The RAST test is a measurement of a specific allergen. The allergen of interest, such as short ragweed, is bound to the disc and reacts only with the short ragweed IgE in the sample. After the initial incubation, non-specific IgE antibody and other proteins are removed by washing. Radioactively-labeled anti-IgE is then added and allowed to incubate overnight thereby forming a radioactive complex with the specific IgE. The radioactivity is then compared to a standard. The Phadebas RAST reference system is composed of four dilutions of a pooled serum from patients highly allergic to birch antigen. Initially, reference A, the concentrated serum in this system, was assigned the arbitrary value of 50 Phadebas RAST units (PRU), and reference D, a 1-50th dilution of reference A, was assigned the arbitrary value of 1 PRU. The readability of the test was 1 to 100 PRU. More recently, the references have been improved extending readability to about 300 PRU (0.35-100 PRU). Serums with scores below reference D (originally 1 PRU and now 0.35 PRU) have been regarded as negative.

The RAST test is of particular utility in the management of pediatric allergic patients in whom end point skin test titrations are difficult to perform and which may be emotionally traumatic to both the child and his parents.

Despite the great value of the RAST test, it is deficient in that there is a very high degree of false negative results. For example, Deuschl and Johansson, Specific IgE Antibodies in Nasal Secretion from Patients with Allergic Rhinitis and with a Negative or Weakly Positive RAST on the Serum, Clinical Allergy, March 1977, reported on studies of 18 patients in whom a diagnosis of allergic rhinitis had been made by history and confirmed by intra-dermal skin testing and nasal provocation study. None of these patients were positive by the RAST test according to the cutoff value for positive result as determined by the Phadebas RAST curve. Many clinicians have had the disappointing experience of submitting known allergic serum for RAST testing and having the results returned to them as negative.

It is the object of this invention to provide a modified RAST test whose results can be used to determine a safe initial immunotherapy dosage and also an optimum dosage. It is also the object of this invention to provide a modified RAST test in which the number of false negatives is greatly reduced. This and other objects of the invention will become apparent to those skilled in the art from the following detailed description.

SUMMARY OF THE INVENTION

This invention relates to an improved allergy test and more particularly to an improved RAST test in which the standard against which activity is measured is the PRIST reference standard as a positive control and against an appropriate negative control.

DESCRIPTION OF THE INVENTION

In accordance with the present invention sera are compared in the RAST test to determine antibody concentration. It has previously been shown that all reaginic sera, when serially diluted, give parallel curves through three ten-fold dilutions. These results, when plotted on a log-to-log scale, are linear. It has been appreciated that the PRIST reference standard also produces a dose response curve parallel to the various reaginic sera and can ideally serve to develop a reference curve for determining both total IgE levels in the PRIST test and specific antibody titers in the RAST test. As the PRIST reference standard undergoes a thousand-fold change in concentration, i.e. 3 $\log_{10}$, the radioactivity bound changes 32 times, i.e., 1.5 $\log_{10}$. For every four-fold change in IgE concentration, there is a corresponding doubling or halving of the amount of radioactivity bound. To state this relationship in another way, the square root of the change in concentration gives the expected change in the amount of radioactivity bound. For example, a 100-fold change in concentration of antibody is associated with a 10-fold change in bound radioactivity and a 25-fold change in concentration would be associated with an expected 5-fold change in bound radioactivity.

In the method of this invention, the serum is evaluated against a negative and a positive control in a modified RAST test. Previously, a positive RAST result has been defined as a RAST score twice that of a negative control. The aforementioned Deuschl and Johansson observed that a five-fold dilution of reference D gave scores more than twice those of negative controls and established 0.2 PRU as a new lower limit for a positive score. Experience has now shown that the range of positive activity with the new reference D can be extended by significant dilution and still obtain scores twice that of negative controls, thereby eliminating a significant percentage of false negative results.

An appropriate negative control is used in the instant test. The negative control can be newborn human cord serum or serum from non-allergic patients or even serum from allergic patients since not every atopic patient is allergic to all antigens. The instant test is carried out with the serum to the point of determining the amount of bound radioactivity of the PRIST reference preparation. To avoid confusion with other test results, these activity units will be called NRU's. Sera with the same binding ability as 25 units of IgE (a fourfold dilution of the PRIST reference material containing 100 units of IgE) were assigned 25 NRU. The positive reference is put through several dilutions to establish a reference curve and sera are assigned arbitrary values based on the diluted references.

The Phadabes RAST test is run for a fixed period of time and the bound radioactive counts recorded are compared to the reference standard counts. However, radioimmunoassays vary from day to day, and by using a fixed time point, the obtained counts vary each time the test is performed. To eliminate this effect, the instant test is performed until a fixed number of counts has been obtained with the positive control and then the tested serum and negative control are run for the same time period. When the patient's serum bound counts are more than twice the binding of the negative control, the serum is deemed positive. In this manner, the test readability has been extended to 0.04 NRU.

The modified RAST test described above has the advantage of being of much more use than the RAST test now being used. The number of false negative results has been greatly reduced. Additionally, the modification described above permits the clinician to establish initial immunotherapy dosage for the appropriate antigen without having to begin at a very dilute concentration and then gradually increase the hypersensitization dosage. The mathematical relationships described above and the NRU values establish a basis for creating six classes of positive scores between 0.04 and 100 NRU. The amount of radioactivity bound in each class is double that of the previous class.

It has been determined that each NRU is equivalent to a passive cutaneous transfer (PK) titer of 100. Thus, 100 NRU is equivalent to a 10,000 PK titer and 0.04 NRU is equivalent to a PK titer of 4. Mathematically, the relationship can be expressed as Titer=(specific binding counts/non-specific binding counts)$^2$. For example, if the serum tested against the antigen of interest gives 50,000 counts and the non-specific binding is 500 counts, the PK titer is 10,000, i.e., $(50,000/500)^2$. The initial immunotherapy dosage is established based on the following table.

| Class | PK Titer | Dosage, w/v |
|---|---|---|
| 1 | 4–9 | 1–200 |
| 2 | 10–39 | 1–500 |
| 3 | 40–159 | 1–2,000 |
| 4 | 160–639 | 1–8,000 |
| 5 | 640–2499 | 1–32,000 |
| 6 | 2,500–10,000 | 1–125,000 |
|   | over 10,000 | 1–500,000 |

The initial dose can be established to a highly specific amount in accordance with the equation dose (in protein nitrogen units)=1000/PK titer but the foregoing ranges are more facile to employ.

There has been no significant systemic reactions in over 50,000 therapeutic antigen doses despite the fact that most of the initial doses were at concentrations greater than 1–8000.

One hundred children, aged 3 to 14, with either a positive history of allergy or recurrent serious otitis media were tested for total circulating IgE antibody. The geometric means serum IgE in this group was 88 units. 300 adults, 15 years of age and above, with signs and symptoms suggestive of allergic disorders were found to have a geometric means serum of 98 units. Prior to the start of this study, a geometric means value of 15 units per milliliter was obtained in 15 nonatopic employees. In the entire group of 400 patients, the range of IgE scores varied from a low of 3 to a high of 1600 units. Just under 50% of the patients had IgE scores above 100 units.

The 400 patients were studied by the modified RAST test of this invention against a panel of 10 antigens: June grass, short ragweed, maple tree, alternaria, house dust, house dust mite, cat epithelium, dog epithelium, English plantain and milk. When the patient's history indicated that other antigens should be substituted or added, this was done. At least one RAST result was recorded as positive in 90% of the 400 patients tested and 82% of the patients were positive to two or more antigens. 90% of the positive scores had titer ranges in Classes 1, 2 and 3. 50% of the positive scores were within Class 1 alone and less than 1% of the positive scores were found in Class 6. Most of the antigens tested gave a similar percentage of positive scores approaching 60% but only 30% of the tests against house dust antigen were positive. In fact, no patient had a high concentration of house dust IgE antibody above Class 3. On the other hand, 45% of the sera tested against house dust mites were positive. In several sera, there was mite IgE antibody concentrations in Class 5 and 6. The total amount of circulating IgE antibody could be correlated with the RAST results in a general way, i.e., patients with the highest concentration of specific antibody all had total IgE levels of at least 300 units. The presence of a high total circulating IgE did not necessarily mean that any specific RAST titer would be high. In some patients with an IgE level of 750 units, no particular IgE antibody was found with a concentration higher than Class 1. Therefore, an elevated IgE represents a widespread diversity in the number of specific antibodies present in the serum. On the other hand, many patients with serum IgE levels below 100 units had antibody titer elevations to a limited number of antigens.

The results summarized above are consistent with findings previously reported in the literature. It should be noted that more than 60% of the positive scores in the above study were negative when the standard RAST test is effected.

Various changes and modifications can be made in the method of this invention without departing from the spirit and scope thereof. The embodiments disclosed herein were for the purpose of illustrating the invention but were not intended to limit it.

What is claimed is:

1. A method of determining the sensitivity to a specific allergen which comprises
    (a) determining the measurable bound radioactivities for a given unit of time of a first sample of known total IgE concentration and a plurality of dilutions thereof by effecting radioallergosorbent (RAST) tests on said first sample and each of said dilutions and measuring bound radioactivity for said unit of time;

(b) effecting a RAST test on a second sample of known total IgE concentration to determine the length of time required to measure a given amount of bound radioactivity;

(c) effecting a RAST test on a test sample and measuring bound radioactivity for said length of time;

(d) effecting a RAST test on a negative control sample and measuring bound radioactivity for said length of time;

(e) determining whether said test sample is specific allergen positive by comparing the measured bound radioactivities of said test sample with said negative control sample, said test sample being positive when said former measurement is more than double the latter measurement; and (f) comparing the measured bound radioactivities of positive test sample with said first sample of known total IgE content and dilutions thereof.

2. The method of claim 1 wherein the concentration of said second sample is the same as the concentration of said first sample and wherein said given amount of bound radioactivity is the amount of bound radioactivity determined for said first sample in step (a).

3. The method of claim 2 wherein immunotherapy is effected and the initial immunotherapy dosage is determined in accordance with said step (f) comparison, the magnitude of said dose being inversely proportional to the magnitude of said step (c) measurement.

4. The method of claim 3 wherein the range of measured bound radioactivity determined in step (a) is divided into a plurality of classes, the amount of radioactivity bound in each class being double that of a previous class and each class having an initial immunotherapy dosage assigned thereto.

5. A method of establishing a safe initial immunotherapy dosage level for a specific allergen which comprises effecting a Radioallergosorbent test for said allergen and selecting an initial hypersensitization therapy dosage level based thereon.

6. The method of claim 5 wherein said selecting comprises identifying which of a plurality of test result ranges the result of said test falls within and identifying the dosage level preassigned to the determined range.

7. A method of determining the passive cutaneous transfer titer of an allergic serum by in vitro testing which comprises determining the specific radioactivity count of said serum by a radioallergosorbent test for the desired antigen and, determining the nonspecific bound radioactivity count of said serum.

* * * * *